(12) United States Patent
Mason

(10) Patent No.: US 7,661,430 B2
(45) Date of Patent: Feb. 16, 2010

(54) ANTIMICROBIAL DENTAL APPLIANCES INCLUDING MOUTHGUARDS AND MOUTHPIECES

(76) Inventor: Richard Mason, 21 Crosshill Rd., Newton, MA (US) 02459

( * ) Notice: Subject to any disclaimer, the term of this patent is extended or adjusted under 35 U.S.C. 154(b) by 93 days.

(21) Appl. No.: 11/601,995

(22) Filed: Nov. 20, 2006

(65) Prior Publication Data

US 2007/0267029 A1    Nov. 22, 2007

Related U.S. Application Data

(60) Provisional application No. 60/801,653, filed on May 19, 2006.

(51) Int. Cl.
    *A61F 5/56* (2006.01)
    *A61C 5/14* (2006.01)
    *A61C 3/00* (2006.01)
(52) U.S. Cl. ............... 128/848; 128/859; 128/861; 128/862; 433/6
(58) Field of Classification Search ............ 128/859, 128/861, 862; 428/408; 433/8, 6, 7, 18, 433/19, 24; 600/240; 602/902; 524/403, 524/430, 437; 523/105
See application file for complete search history.

(56) References Cited

U.S. PATENT DOCUMENTS

| | | |
|---|---|---|
| 3,107,667 A | 10/1963 | Moore |
| 3,603,306 A | 9/1971 | Bonin |
| 3,844,281 A | 10/1974 | Shamlian |
| 3,929,548 A | 12/1975 | Shamlian |
| 4,136,689 A | 1/1979 | Shamlian |
| 4,411,041 A | 10/1983 | Braga |
| 4,476,590 A | 10/1984 | Scales et al. |
| 4,664,109 A | 5/1987 | Rasocha |
| 4,862,903 A | 9/1989 | Campbell |
| 5,019,096 A | 5/1991 | Fox et al. |
| 5,031,611 A | 7/1991 | Moles |
| 5,062,422 A | 11/1991 | Kinkade |
| 5,203,324 A | 4/1993 | Kinkade |
| 5,282,462 A | 2/1994 | Kudo |
| 5,305,741 A | 4/1994 | Moles |
| 5,474,797 A | 12/1995 | Sioshansi et al. |
| 5,614,568 A * | 3/1997 | Mawatari et al. ............. 523/122 |
| 5,620,011 A * | 4/1997 | Flowers ..................... 128/859 |
| 5,626,128 A * | 5/1997 | Bradley et al. ......... 128/200.26 |
| 5,638,811 A | 6/1997 | David |
| 5,688,492 A | 11/1997 | Galley et al. |
| 5,701,885 A | 12/1997 | Hale |
| 5,865,170 A * | 2/1999 | Moles ................... 128/201.26 |
| 5,958,440 A | 9/1999 | Burrell et al. |
| 5,980,868 A | 11/1999 | Homola et al. |
| 6,079,411 A | 6/2000 | Giovanni |
| 6,123,925 A | 9/2000 | Barry et al. |

(Continued)

FOREIGN PATENT DOCUMENTS

CN    1451811 A    10/2003

(Continued)

*Primary Examiner*—Patricia M Bianco
*Assistant Examiner*—Ophelia Hawthorne

(57) ABSTRACT

The present invention provides for a dental appliance, mouthguard and/or divers mouthpiece using an anti-microbial composition that combines the use of an elastomeric polymer composition with micronized or submicron sized particles of metal or organo/inorgano metal complexes. In addition, the use of an anti-microbial composition for use with a diver's air delivery hose to prevent breathing of contaminated air is also described.

12 Claims, 1 Drawing Sheet

U.S. PATENT DOCUMENTS

| | | |
|---|---|---|
| 6,224,983 B1 | 5/2001 | Sodervall et al. |
| 6,257,239 B1 | 7/2001 | Kittlesen et al. |
| 6,267,590 B1 * | 7/2001 | Barry et al. .................... 433/8 |
| 6,379,712 B1 * | 4/2002 | Yan et al. .................... 424/618 |
| 6,491,036 B2 | 12/2002 | Cook |
| 6,536,424 B2 | 3/2003 | Fitton |
| 6,539,943 B1 | 4/2003 | Kittlesen et al. |
| 6,553,996 B2 | 4/2003 | Kittlesen et al. |
| 6,581,604 B2 | 6/2003 | Cook |
| 6,626,180 B1 | 9/2003 | Kittlesen et al. |
| 6,675,806 B2 | 1/2004 | Kittlesen et al. |
| 6,691,710 B2 | 2/2004 | Kittlesen et al. |
| 6,735,149 B2 | 5/2004 | Pierot |
| 6,820,623 B2 | 11/2004 | Cook |
| 6,924,325 B2 | 8/2005 | Qian |
| 7,183,003 B2 * | 2/2007 | Leu et al. .................... 428/408 |
| 2006/0207611 A1 * | 9/2006 | Anonsen .................... 128/859 |

FOREIGN PATENT DOCUMENTS

| | | |
|---|---|---|
| JP | 03002113 A2 | 1/1991 |
| JP | 06122606 A2 | 5/1994 |
| JP | 06122617 A2 | 5/1994 |
| JP | 11019238 A2 | 1/1999 |
| JP | 11169387 A2 | 6/1999 |
| JP | 11178843 A2 | 7/1999 |
| JP | 2000288108 A2 | 1/2000 |
| WO | WO9822186 A1 | 5/1998 |

* cited by examiner

ANTIMICROBIAL DENTAL APPLIANCES INCLUDING MOUTHGUARDS AND MOUTHPIECES

PRIORITY

This patent application claims priority to pending Provisional application No. 60/801,653 filed May 19, 2006; titled "ANTIMICROBIAL DENTAL APPLIANCES INCLUDING MOUTHGUARDS AND MOUTHPIECES"

FIELD OF INVENTION

This invention is related generally to dental appliances, mouthguards and diving mouthpieces that include antimicrobial agents, specifically micronized or sub-micron sized metal particles for such an application.

BACKGROUND OF INVENTION

This invention relates to dental appliances and mouthguards, and more particularly to dental appliances and mouthguards with antimicrobial additives to resist the growth of fungus, yeast, viruses, bacteria and the like which may cause illness, infection or gum disease.

It is well known that athletes who participate in contact sports wear mouthguards to protect their teeth from sharp blows as well as to protect the head and temporomandibular joint from possible concussion. Mouthguards are common, for example, in football, hockey, soccer, rugby, and boxing. Mouthguards may be considered a subgroup of dental appliances.

There is also a trend for athletes, such as body-builders, weight-lifters, baseball batters, golfers, football players, hockey players, and bowlers to wear dental appliances to prevent the clenching of their teeth during exertion which results in hundreds of pounds of compressed force exerted from the lower jaw onto the upper jaw. Teeth clenching may also occur in bruxing and child birthing. Clenching can result in headaches, muscle spasms, damage to teeth and injury to the temporomandibular joint as well as pain in the jaw. Thus, dental appliances have been created having posterior pads to be positioned between the upper and lower teeth to prevent clenching and damage to one's teeth and jaw structures.

It also is well known that there are dental appliances for a myriad of other uses. Splints, which resemble mouthguards, are used for bleaching of teeth, while other appliances may be used to control breathing and snoring. Dentists also use appliances in administering to teeth during dentistry.

It is well known that the mouth and articles that are repeatedly placed into the mouth may allow for the growth of fungus, yeast, viruses, and bacteria. One method for treatment to resist such growth includes sterilization. Washing or application of antimicrobial agents are also other methods of cleansing appliances.

Scuba-diving mouthpieces of various kinds have been known and used for many years. Despite advances in recent years, there are many problems and shortcomings with scuba-diving mouthpieces as shown in the prior art. One of the most common problems relates to repeated use and improper cleansing or removal of bacteria from diving mouthpieces.

Divers, by necessity, are required to utilize a mouthpiece which is, in most cases, an elastomeric polymer member (such as molded from liquid silicone rubbers) having, on one (or back) end, a portion for fitting against the gums of the diver, and internal members which require the diver to clamp their teeth onto the mouthpiece during the diving excursion. On the other (or front) end the mouthpiece is attached by a means to a diving regulator through a hose and therefore can be difficult to sterilize, wash or apply antimicrobial agents.

The regulator delivers compressed air to the diver from a compressed air tank. The diver breathes this air through the opening portion of the mouthpiece, receiving the air through an air hose and thereby breathes in any air contaminated with fungus, yeast, viruses and bacteria present within the air delivery opening.

Examples of scuba-diving mouthpieces are those shown in U.S. Pat. No. 3,107,667 (Moore), U.S. Pat. No. 3,844,281 (Shamlian), U.S. Pat. No. 3,929,548 (Shamlian), and U.S. Pat. No. 4,136,689 (Shamlian), and U.S. Pat. No. 5,305,741 (Moles) U.S. Pat. No. 5,031,611 (Moles) and U.S. Pat. No. 5,620,011 (Flowers). These U.S. patents are herein incorporated by reference.

There is a need for an antimicrobial dental appliance, mouthguard and/or diving mouthpiece such that the antimicrobial is integral to the materials and construction of the device itself, thereby resizing or eliminating growth of fungus, yeast, viruses and bacteria. The anti-microbial dental appliance may be used singularly or in conjunction with sterilization, washing or with the application of antimicrobial agents.

DESCRIPTION OF PRIOR ART

U.S. Pat. No. 3,107,667, issued to Moore describes a customizable mouthpiece manufactured by taking dental impressions in wax and creating an enamel or other hard material in order to form a proper impression in a hot rubber composition. When the rubber is cooled the dental impression remains and is a custom fit for the user.

U.S. Pat. No. 3,929,548 issued to Shamlian describes a method of customizing the retaining portion of a mouthpiece of an underwater breathing apparatus to the bite of the individual user by heating a blank of thermoplastic material until it is at a temperature sufficient to render the blank thermoplastic. The mouthpiece is then placed in the mouth of the user while in a thermoplastic state and the user bites down on the thermoplastic material to cause the blank to flow and to form an impression of the users bite. The impressed blank is cooled whereby the retainer portion of the mouthpiece is customized to the bite of the user.

PCT Publication WO9822186A1 issued to Stier describes an emergency breathing device with a resilient mouthpiece and a valved body for receiving a hose coupling and a seal whereby gas pressure in the hose closed the seal. Squeezing pressure from opposite sides of the mouthpiece exerts a force on the valve actuator, opening the seal and allowing a breathable gas to flow from the hose into the mouthpiece.

U.S. Pat. No. 6,536,424 issued to Fitton, describes a mouthpiece with a continuous wall with anterior and posterior sections. The anterior and posterior sections have an inner surface that conforms to an anatomy of a user's upper and lower dental arches and retaining wings substantially conforming to the users mouth.

U.S. Pat. No. 3,603,306 issued to Bonin, describes a snorkel for use by divers or the like having a mouthpiece with an orifice for a breathing tube that is offset to the side allowing for the tube to be curved substantially along the users face to minimize friction and drag.

U.S. Pat. No. 3,844,281 issued to Shamlian, describes a mouthpiece to be used in combination with underwater breathing apparatus that supplies breathable gas to a subject through a conduit whereby the mouthpiece is a pliable flange means for insertion between the lips and the outer frontal surface of the teeth of the user. A pair of tabs located on opposite sides of the breathing hole that engage only the several top and bottom teeth behind the front teeth whereby the retaining means of the mouthpiece is customized to the bite of the individual user. The mouthpiece is fabricated of a material that is less plastic than the customized portion of the mouthpiece.

U.S. Pat. No. 4,862,903 issued to Campbell, describes a mouthpiece for a second stage breathing gas regulator with a portion having a curved upper lip flange adapted generally for conforming to the interior region of a user's mouth between the upper teeth and the user's upper lips and a curved lower lip flange adapted generally for conforming to the interior region of a user's mouth between the user's lower teeth and the inner lower lips respectively. The mouthpiece has an upper interior web anatomically shaped for contact with at least part of the inside surfaces of at least the frontal upper teeth of a user's palate U.S. Pat. No. 5,062,422 issued to Kinkade, describes a mouthpiece oriented for an overbite with wing members having a taper such that the one end that is farther from the orifice is smaller than the second end nearer the orifice.

U.S. Pat. No. 5,203,324 issued to Kinkade, describes a mouthpiece oriented for an overbite with wing members having a taper such that the one end that is farther from the orifice is smaller than the second end nearer the orifice and where the wing members having a laterally extending surface bounded on either side thereof by substantially vertical curved walls for contacting the lateral surfaces of the user's cuspids and bicuspids.

U.S. Pat. No. 5,701,885 issued to Hale, describes a pressure equalizing scuba diver mouthpiece with a fluid equalizing passageway such that when a user changes contact position on the mouthpiece the fluid flows from one bitewing to the other so that the pressure is equalized.

U.S. Pat. No. 4,664,109 issued to Rasocha, describes a mouthpiece with a pliable lip flange for insertion between the lips and the outer frontal surface of the teeth And a plurality of lugs connected to and extending from said lip flange on opposite sides of said hole for disposition between the biting surfaces of the teeth.

Also described is a multiplicity of individual, spaced apart, upstanding, resilient projections on the upper and lower sides of the lugs with the distal ends of the projections providing a multiplicity of spaced apart planar surfaces for abutment with the biting surfaces of said teeth.

U.S. Pat. No. 6,820,623 issued to Cook, describes a customizable athletic force absorbing mouthguard having a u-shaped base with upstanding labial and lingual walls forming a channel for the teeth of a user comprised of low-density polyethylene with tactifier resin to improve durability, retention and fit of the mouthguard.

U.S. Pat. No. 6,626,180 Kittlesen, et. al., describes a composite performance enhancing and force absorbing mouthguard having a U-shaped base with upstanding labial and lingual walls forming a channel with a softenable, customizable wall and base material to custom fit the mouth of a user and forming the labial and lingual walls and the base. Two elastomer traction pads located posteriorly below the base and a pair of disconnected anterior elastomer braces forms a gap there between to permit adjustment of the braces to conform to irregularities of anterior teeth and to custom fit the channel to the mouth of a user.

U.S. Pat. No. 6,691,710 issued to Kittlesen, et. al., describes a composite performance enhancing and force absorbing mouthguard having a U-shaped base with upstanding labial and lingual walls forming a channel with a nonsoftenable, flexible framework of posterior occlusal plates in the base. Two hard durable bite wedges are located posteriorly along the occlusal plates with each wedge being thicker posteriorly than anteriorly. On top of the two bite wedges are elastomer traction pads and a pair of disconnected anterior impact braces. Each brace permits adjustment of the braces to conform to irregularities of anterior teeth of the user a softenable, customizable wall and channel to fit the channel of the mouthguard to the mouth of a user.

U.S. Pat. No. 6,675,806 issued to Kittlesen, et. al., describes a composite performance enhancing and force absorbing mouthguard with a softenable, customizable wall and base material to custom fit the mouth of a user.

U.S. Pat. No. 6,553,996 issued to Kittlesen, et. al., describes a dental appliance for a mouth having antimicrobial characteristics comprising an antimicrobial additive in an occlusal pad to be placed on teeth within the mouth.

U.S. Pat. No. 6,539,943 issued to Kittlesen, et. al., describes a dental appliance with a pair of posterior occlusal pads and a framework extending from the pads upwardly and inwardly forming an arch with each pad having a bite plate of hard very durable material and a softenable, impressionable material encapsulating the bite plate, the framework and substantially the pads.

U.S. Pat. No. 6,581,604 to Cook, describes a customizable athletic force absorbing mouthguard having a u-shaped base with upstanding labial and lingual walls forming a channel for the teeth of a user comprised of low-density polyethylene, further comprising an antimicrobial additive in the low-density polyethylene.

U.S. Pat. No. 6,257,239 issued to Kittlesen, et. al., describes a performance enhancing and force absorbing dental appliance with a pair of posterior occlusal pads and an arch connecting the pads; and an anti-microbial additive in the pads and arch.

U.S. Pat. No. 6,491,036 to Cook describes a customizable athletic force absorbing mouthguard having a u-shaped base with upstanding labial and lingual walls forming a channel for the teeth of a user comprised of low-density polyethylene with a nucleating agent to securely shrink and fit the mouthguard.

U.S. Pat. No. 5,282,462 issued to Kudo describes a mouthpiece of a regulator to supply air from a cylinder into a cavum oris of a diver with the mouthpiece having a tube which abuts against an outer side of the cavum oris of the diver when the mouthpiece is worn by the diver. The tube is connected with a demand regulator unit and a pair of teeth grips extending from said tube toward molar teeth in the cavum oris of the diver so as to be bitten and held by the molar teeth. The teeth grips are integrally provided with connecting rods which are inserted into the tube of the mouthpiece with each connecting rod connected to the tube so as to be integral with said tube. The connecting rods are slightly longer than the tube such that each of the teeth grips is to the outside of the tube. Biting portions are laminated against the molar teeth that are vertically abutted and connected to the connecting rods.

U.S. Pat. No. 5,638,811 issued to David describes an anatomical mouthpiece in two sections that includes a first section having an connection piece that is connectable to a gas source. A second section two vertical vestibules matching an anatomical shape of the mouth of the user. The second section is made of biocompatible and flexible thermoplastic material which is formable at standard body temperature in a mouth area.

U.S. Pat. No. 5,865,170 issued to Moles describes a scuba-diving mouthpiece for customizing for a particular diver including means for gripping a diver's teeth having: (1) a front member extending from a proximal in-mouth end to a distal outside end and forming a horizontal passageway from the distal end to the proximal end; and (2) a U-shaped formable back member having (a) a forward middle portion secured to the front member proximal end in position for formable custom moldable engagement with the diver's forward teeth and (b) a pair of leg portions extending from the middle portion rearwardly to pass between the diver's molars and terminate at the rear of the mouth, each leg portion having inner and outer upstanding flanges and a substantially horizontal bite portion extending therebetween, the bite portion having formable custom-moldable upper and lower surfaces and the flanges having upwardly-extending and downwardly-extending flange portions with upper and lower edges, respectively, and inside surfaces spaced for formable custom-moldable engagement with opposite side surfaces of the user's teeth, said outer flanges extending forward to merge with the forward middle portion, the improvement comprising: * the inner upstanding flange of each leg portion rearwardly terminating substantially lateral to the diver's first molar; * the outer flange of each leg portion forming a concave outside surface on the leg portion, the concave surface having a nadir line substantially along and adjacent to the horizontal bite portion; * the outer flange of each leg portion rearwardly terminating forward of the diver's second molar * the horizontal bite portion extending beyond the diver's second molar; * the bite portion having, at positions adjacent to the inner flange, a first width; and * the bite portion having, at positions beginning immediately rearward of the inner flange, a second width which is no greater than the first width.

U.S. Pat. No. 5,305,741 to Moles, describe a scuba-diving mouthpiece for customizing for a particular diver including a U-shaped formable, custom moldable upper and lower surfaces and having flanges upwardly and downwardly extending. These flange portions engage with opposite side surfaces of the user's teeth with the outer flanges extending forward to merge with the forward middle portion.

U.S. Pat. No. 5,031,611 to Moles describes a scuba-diving mouthpiece with the bite members having the diver's dental impressions therein to form a major customized tooth engagement providing intimate tooth contact to the full extent of the diver's molars while the diver's mouth is in a relaxed, partially-opened position, thereby eliminating diver fatigue.

U.S. Pat. No. 6,735,149 issued to Pierot, describe a mouthpiece for a snorkel or diving regulator, adapted to fit in the mouth of a diver or swimmer having at least one transducer buzzer for transmitting the vibrations of said membrane towards teeth of the diver or swimmer, as an aid to underwater communications.

U.S. Pat. No. 4,136,689 issued to Shamlian describes a retainer for the mouthpiece of an underwater breathing apparatus for gripping between the user's upper and lower teeth essentially only on either opposite side of the central front teeth with the upper and lower teeth of the user spaced apart to facilitate breathing through the breathing tube. The retainer is being made of a material which is thermoplastic at an elevated temperature compatible with use within the mouth of the user and which is moldable while in a thermoplastic state by the bite of the user so as to flow to form an impression of the bite of the user in the material upon cooling thereof, whereby each retainer of the mouthpiece can be customized to the bite of the individual user.

U.S. Pat. No. 3,844,281 issued to Shamlian describes a mouthpiece for insertion between the lips and the outer frontal surface of the teeth of the user with a breathing hole for passing gas in a substantially unobstructed flow path into the mouth and through the teeth of the subject. The flange being held in the users mouth only the several top and bottom teeth behind the front teeth.

U.S. Pat. No. 6,079,411 issued to Garofalo describes a mouthpiece with orthodontic tooth grip for divers comprising two hollow bodies made of very thin and very elastic material and filled with a very fluid material. Garofalo teaches a high elasticity material and filling the hollow bodies with a very fluid material whereas the cavity and fluid is contained within the hollow bodies, but not dispensed to the diver.

U.S. Pat. No. 5,620,011 issued to Flowers describes an improved mouthpiece apparatus wherein the tooth contact area provides a slit into a hollow chamber for the insertion of a flavorful gel substance for the divers enjoyment. Flowers does not teach toward an anti-microbial artificial saliva.

U.S. Pat. No. 5,019,096, to Fox, et. al., assigned to the Trustees of Columbia University, describes a method for making an infection-resistant material comprising incorporating an effective amount of an antimicrobial agent in a matrix comprising a polymeric component selected from the group consisting of biomedical polyurethanes, biomedical silicones, biodegradable polymers and combinations thereof, wherein the matrix is effective to provide controlled release of the antimicrobial agent at a level sufficient to suppress infection when in contact with fluids, and wherein the antimicrobial agent includes synergistically effective amounts of a silver salt and a biguanide. Biguanide (PHMB) is the generic name of one of the more popular non-chlorine, non-bromine chemical sanitizers used in swimming pools. The main advantage is that no chlorine or bromine is required and there is little chemical odor. Biguanide is an effective bactericide and can replace chlorine or bromine, in that function. However, chlorine or bromine are also oxidizing agents that can destroy organic contamination: biguanide cannot destroy organic contamination and, therefore, concentrated hydrogen peroxide must be added to the swimming pool on a regular basis. A disadvantage of biguanide is the development of biguanide-resistant microorganisms, after a few years of product usage.

U.S. Pat. No. 6,924,325, to Qian, Xuejun, assigned to Kerr Corporation, describes a dental composition comprising a silver-zinc containing glass, at least one monomer having at least one ethylenically unsaturated group, a polymerization initiator system and optionally a finely divided filler.

U.S. Pat. No. 4,411,041, to Braga, Renato, unassigned, describes a toothbrush comprising a handle and a head having a surface and fitted with bristles, at least that part of the head's surface which carries the bristles being coated with silver whose bactericidal properties, when contacted with water, are transferred by the water to the bristles by the ions of silver possessed within the silver, wherein the silver coating is applied before insertion of the bristles, said coating being also applied to the sides of the holes in which the tufts of the bristles are fitted to provide a sterilization action on the bristles and within the spaces among the base of the bristles, and between the sides of said holes and the bristles in such a way as to avoid proliferation of bacteria on the bristles from their base portions to the tips thereof U.S. Pat. No. 4,476,590, to Scales, et. al., assigned to National Research Development Corporation, describes an endoprosthetic implant comprising a permanent implant structure formed of a substantially bioinert structural material providing permanent mechanical integrity to the implant, wherein a bioerodible metallic silver component is deposited to form a surface coating 25 to 500 Angstroms in thickness on said permanent implant structure and provides in vivo a sustained release of silver ions in a concentration sufficient to provide a localized anti-microbial effect but insufficient to cause significant damage to connective tissue.

U.S. Pat. No. 5,958,440, to Burrell, et. al., assigned to Westaim Technologies, Inc., describes an anti-microbial form of silver material, comprising: silver metal, or an alloy or compound thereof, in a crystalline form having sufficient atomic disorder such that the material, in contact with an alcohol or a water based electrolyte, releases atoms, ions, molecules or clusters containing silver on a sustained basis at a concentration sufficient to provide a localized anti-microbial effect, said material having a positive rest potential, when measured against a saturated calomel reference electrode, in 1M potassium hydroxide, wherein the atomic disorder in the material provides irregularities in surface topography and inhomogeneities in structure on a nanometer scale and is caused by high concentrations of one or more of point defects in a crystal lattice, vacancies, line defects, dislocations, interstitial atoms, amorphous regions and grain and sub grain boundaries, relative to a normal ordered crystalline state for silver metal, and wherein the anti-microbial effect is sufficient to generate a zone of inhibition of greater than 5 mm.

U.S. Pat. No. 5,474,797, to Sioshansi, et. al., assigned to Spire Corporation, describes a method for depositing a bactericidal coating on a polymeric biomedical implant by ion beam assisted deposition, comprising introducing a polymeric biomedical implant into an evacuated chamber, evaporating a bactericidal evaporant within the chamber to form a vapor of said evaporant proximate to said polymeric biomedical implant, introducing accelerated ions into the chamber, and bombarding at least a portion of said polymeric biomedical implant with the accelerated ions to drive said evaporant into said polymeric biomedical implant to form the bactericidal coating.

U.S. Pat. No. 6,224,983, to Sodervall, et. al., assigned to Ad Tech Holdings Limited, describes an article that resists microbial growth prepared by a method which comprises activating at least a portion of the surface area of an article which article is constructed of a nonconducting material selected from the group consisting of latex, polystyrene, polyester, polyvinylchloride, polyurethane, ABS polymers, polycarbonate, polyamide, polytetrafluoroethylene, polyimide and synthetic rubber; followed by chemically depositing a silver layer of 2-2000 angstroms by treating said activated surface with an aqueous solution of at least one salt of silver in the presence of a deposition control agent, said depositing being conducted for only sufficient time to result in said 2-2000 angstroms silver layer; and rinsing in demineralized water and drying.

U.S. Pat. No. 6,123,925, to Barry, et. al., assigned to HealthShield Technologies L.L.C., describes a toothpaste formulation having antimicrobial properties comprising: an antimicrobial agent comprising ceramic particles comprising antimicrobial metal ions; at least one ingredient capable of inactivating the antimicrobial metal ions wherein the antimicrobial agent is disposed within an aqueous based paste or gel forming a barrier layer separating the metal ions from at least one ingredient with metal ions being released imparting substantial antimicrobial action to an oral surface upon contact with the oral surface during normal toothbrushing.

U.S. Pat. No. 5,980,868, to Homola, et. al., and unassigned, describes a composition, comprising a transfer material and a barrier material wherein when the composition is applied to a surface of a tooth it forms a coating on the surface of a tooth the transfer agent binds electrostatically to the surface of the tooth and the barrier material binds to the transfer agent electrostatically bound to the surface of the tooth, and the coating conforms to and fills pits, fissures, cracks, and irregularities present on the tooth surface.

U.S. Pat. No. 5,688,492, to Galley, et. al., assigned to The Boots Company PLC, describes an oral composition suitable for use in oral hygiene or dental treatment comprising an effective amount of an antimicrobial agent in the form of a particulate, non-ion-exchanging, zeolite-free, inert metal oxide, a sparingly soluble metal salt providing antimicrobial metal ions in use and a further material selected from the group consisting of humectants, gelling agents, abrasives, fluoride sources, desensitizing agents, flavorings, colorings, sweeteners, preservatives, structuring agents, bactericides, anti-tartar agents and anti-plaque agents.

Japanese Patent Publication No. JP03002113A2, to Ogawara Akira, assigned to Sanpo Seiyaku KK describes metals of gold, silver and zinc having antibacterial action that are subjected to ion exchange with A, X or Y type zeolite or mordenite using water soluble salts of these metals in order to obtain a composition for an oral cavity containing a zeolite on which a metal having antibacterial action is carried by ion exchange and capable of storing for a long period and exhibiting antibacterial action and action for preventing odor of mouth.

Japanese Patent Publication No. JP2000288108A2, to Miyauchi Tatsuo, assigned to Supatta KK, describes antibacterial metals such as silver, zinc, copper, titanium oxide, and zinc oxide that are closely stuck to a base material of a mask by spattering to form the mask having a metal layer on the surface and a woven fabric layer or a non-woven fabric layer on the back face. When the mask is used, it is worn to cover the nose and mouth like a normal mask.

Japanese Patent Publication No. JP 1178843A2, to Atsumi, et. al., assigned to Sangi Co., describes a composition to prevent the adhesion and growth of bacteria in the oral cavity stably over a long term by applying a constitution that a denture stabilizer is made to contain an inorganic antibacterial agent. In particular, one type of antibacterial metal selected from silver, copper, zinc or the like.

Japanese Patent Publication No. JP11169387A2, to Okubo, et. al., assigned to Japan Electronic Materials Corp., describes a complete denture, an artificial tooth, and a denture comprising a dental resin containing at least an oxidation preventing agent and an inorganic based antibacterial agent containing silver as adhesives.

Japanese Patent Publication No. JP06122617A2, to Sakuma, et. al., assigned to Sangi Co., describes a metal having antibacterial property, especially a metal selected from silver, copper, zinc and platinum that is supported on a ceramic in order to provide a composition for oral hygiene material resistant to heat, capable of keeping the antibacterial property for a long period and safe to human body because the supported antibacterial metal does not dissolve in water.

Japanese Patent Publication No. JP06122606A2, to Yaguchi, et. al., assigned to Fuji Shirishia Kagaku KK, describes a thiosulfato silver complex solution prepared by using silver chloride as the raw material and reacting sodium thiosulfate, sodium sulfite and sodium hydrosulfite therewith. It became clear after measuring MIC (minimal inhibitory concentration) of this antibacterial material that this antibacterial material exhibits an antibacterial activity selective to Gram-negative bacteria.

Japanese Patent Publication No. JP11019238A2, to Furumiko Hishahi, assigned to Kokago Corp KK, describes a composition to prevent propagation of adhering bacteria and reduce a gap on the side of a mask by plating the surface of a synthetic fiber with silver or by forming a mask by using a fiber with evaporated silver.

Japanese Patent Publication No. JP11019238A2, to Uchida, et. al., assigned to Shinagawa Fuel Co; Shinanen Zeomitsuku, describes a preventive composition for periodontal disease comprising an active ingredient powder of an inorganic antimicrobial agent containing an inorganic antimicrobial component such as silver or zinc. It is capable of controlling the proliferation of mouth bacteria and effectively suppressing plaque formation.

Chinese Patent Publication No. CN1451811A, to Mingong, et. al., assigned to Fu Mingong, describes a preventive composition for periodontal disease comprising an active ingredient powder of an inorganic antimicrobial agent containing an inorganic antimicrobial component such as silver or zinc. It is capable of controlling the proliferation of mouth bacteria and effectively suppressing plaque formation.

SUMMARY OF THE INVENTION

It is the object of the present invention to provide a dental appliance, mouthguard and/or divers mouthpiece with an anti-microbial polymeric elastomer comprising micronized metals and in particular micronized or submicron sized silver, including colloidal silver.

This invention is an improvement in a dental appliance, mouthguard and/or divers mouthpiece and, more specifically, an improved scuba-diving mouthpiece of the type that includes a substantially rigid non-formable core that provides a rigid shape to the mouthpiece extending from a proximal in-mouth end toward a position short of a distal outside end and forming part of a horizontal passageway with a U-shaped member that forms the complete mouthpiece of a type with a front portion forming a breathing hole comprising a micronized or submicron particles of metals, specifically silver as an additive to the elastomeric polymer mouthpiece composition.

The dental appliance can include a mouthguard and/or divers mouthpiece which is adapted to lie within the mouth of a person and includes antimicrobial micronized or submicron-sized particles of silver or other metals or metal complexes known to exhibit anti-bacterial or anti-microbial activity incorporated into the resin concentrate prior to molding of the dental appliance. The resin concentrate is an elastomeric polymer composition comprising liquid silicone rubbers, other silicone elastomers, fluorinated elastomers, thermoplastic elastomers, polyurethanes, composites of polyvinyl chloride, polyethylene, polypropylene and copolymers of polyethylene and polypropylene, composites including $C_{60}$ and wherein the elastomeric polymer composition includes micronized or submicron sized particles of metals or metal complexes and wherein the particles may be added before or during a molding process such that the mouthguard and/or divers mouthpiece will permit controlled antimicrobial action from the dental appliance, mouthguard and/or divers mouthpiece to the mouth of the user.

A principle object and advantage of the present application includes the addition of antimicrobial agents such as micronized or submicron sized particles of silver that are integrally formed with the dental appliance, mouthguard and/or divers mouthpiece to resist the growth of fungus, yeast, viruses and bacteria thereon. Such micronized particles may be from colloidal silver particles.

Another object and advantage of the present application is that the antimicrobial agent may be delivered from the dental appliance, mouthguard and/or divers mouthpiece directly into the mouth and over the gums to treat and prevent gum diseases by using a coating such as a silver salt or an enzyme or even biguanide or by inserting the anti-microbial and anti-bacterial solution into a set of hollow bitewings.

Another object and advantage of the present application includes a dental appliance, mouthguard and/or divers mouthpiece with the antimicrobial agent that will not require sterilization or other extensive cleansing to remove or destroy fungus, yeast, viruses and bacteria, but may be used in conjunction with other forms of antimicrobial treatment.

Additionally a further objective of this application is an elastomeric air delivery hose including antimicrobial micronized or submicron sized particles of silver, other suitable metals or metal organo or inorgano-complex particles incorporated into the resin concentrate prior to molding, extruding or formation of the air delivery hose or added during the molding operation, such that the air delivery hose will permit antimicrobial contact with the air passing through the hose.

The present application overcomes many of the problems and shortcomings noted in the prior art and described in detail in the Background of the Invention section. Other objects and advantages will become obvious with the reading of the following specification and appended claims and with a review of the figures.

DETAILED DESCRIPTION

Figure 1A:
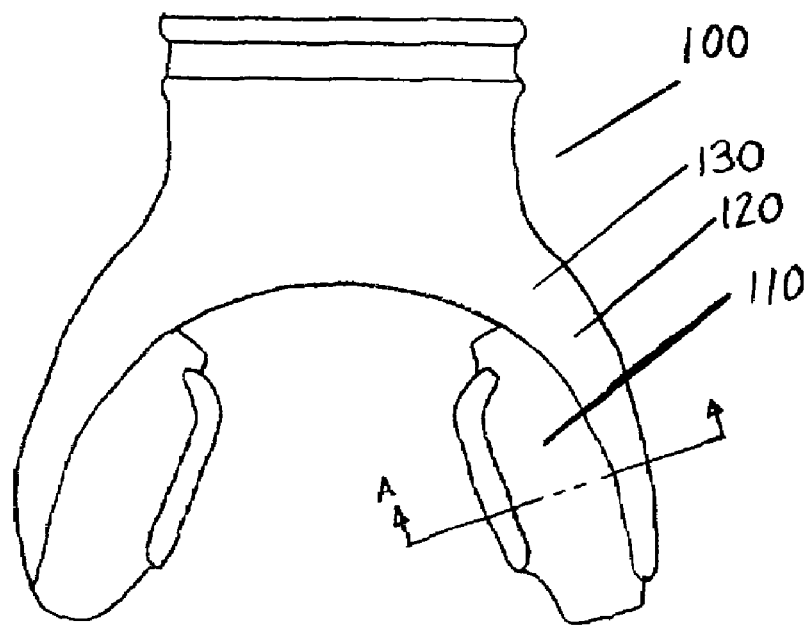
FIG. 1A is an example of a divers mouthpiece with micronized silver.

FIG. 1A is an example of a divers mouthpiece [100] and bitewing [110] with antimicrobial micronized silver [120] matrixed within an elastomeric polymer [130] composition.

Figure 1B:
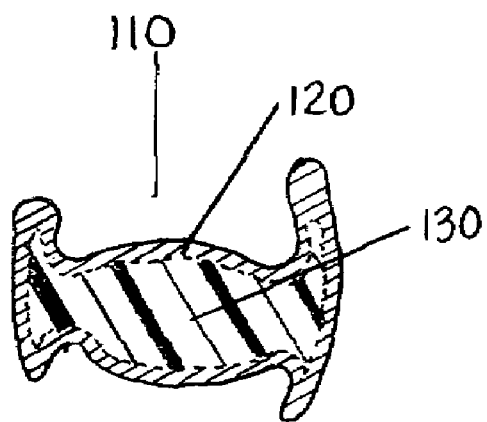
FIG. 1B is a sectional view of a bitewing exhibiting the elastomeric polymer with micronized silver additive.

FIG. 1B is a cross-section of a bitewing [110] exhibiting the elastomeric polymer [130] with antimicrobial micronized or submicron sized metal particles of silver including colloidal silver, other suitable metals or metal organo or inorgano complex particles [120].

The following tables relate to the antimicrobial testing that was performed on prototypes of mouthpieces that include the use of micronized silver. The test method performed was ASTM E2180—Standard Method for Determining the Activity of Incorporated Antimicrobial Agent(s) in Polymeric or Hydrophobic Material. The ASTM method E2180 is the method used "to evaluate (quantitatively) the effectiveness of agents incorporated or bound into or onto mainly flat (two dimensional) hydrophobic or polymeric surfaces".

The test organisms utilized were *Staphylococcus aureus* ATCC 6538 and *Pseudomonas aeruginosa* ATCC 15442. Two separate agar slurries were prepared, one for each organism. The agar slurries contained 1 mL of the test organism (concentration=$7.0 \times 10^8$ cells/mL). 0.85 g NaCl, 0.3 g agar, and 100 mL of deionized water. The final inoculum concentration was equal to $\sim 7.0 \times 10^6$ cells/mL.

All of the samples were prepared in triplicate and aseptically cut into twelve equally sized pieces. One mL of each agar slurry was applied to the prepared samples. Using both sonification and manual vortexing the agar slurry was immediately removed from one set of the control samples and plate counts were performed. The data recovered was designated as '0 hours'.

The remaining set of control samples and the treated material was incubated at 35° C. for 24 hours with the solidified agar slurry intact. The agar slurry was again removed and processed with sonication and vortexing. Plate counts were performed. The data retrieved from this set of samples was designated '24 hours'.

Calculation of 'percent reduction' compares the geometric mean of each time point data set with that of the relevant time point control. The results are shown in Table 1 below.

TABLE 1

Colony forming units (CFU) collected after treated and untreated polymeric mouthpieces were exposed to *Pseudomonas aeruginosa* and *Staphylococcus aureus*. The colony forming units are based on the average of three plate counts.

| Sample Identification | | Contact Time '0 Hours' | | Contact Time '24 Hours' | | Percent Reduction | |
|---|---|---|---|---|---|---|---|
| | | P. aeruginosa CFU/mL | S. aureus CFU/mL | P. aeruginosa CFU/mL | S. aureus CFU/mL | P. aeruginosa | S. aureus |
| #1 | Avg | 50,600,000 | 37,000,000 | 516,000,000 | 312,000,000 | | |
| (Control) | GM | 46,773,514 | 35,481,338 | 501,187,233 | 281,838,293 | | |
| #2 | Avg | | | 63,600,000 | 89,600,000 | 88% | 90% |
| | GM | | | 57,543,993 | 28,183,829 | | |
| #3 | Avg | | | 43,000,000 | 3,800,000 | 95% | 99% |
| | GM | | | 20,893,961 | 1,445,439 | | |

Avg: Average of the three triplicate values

GM: Geometric Mean of the three triplicate values (used to calculate % Reduction)

The control (#1) was for an untreated mouthpiece comprised of silicone rubber. Sample #2 was a separate mouthpiece manufactured using less than 3.5 grams of micronized silver mixed into the silicone rubber prior to injection molding. Sample #3 was another separate mouthpiece manufactured using as much as 3.5 grams of micronized silver mixed into the silicone rubber prior to injection molding. The silver was diluted with the silicone rubber part A used for injection molding. Part B of the silicone rubber used for silicone rubber molding did not have silver added. The micronized silver had been supplied in a tube which included a polysynthetic oil base, such as provided by Arctic Silver. In other words, the concentration of micronized silver were significantly lower in sample #2 then in sample #3. One such manufacturer of micronized silver is Arctic Silver. They produce micronized silver compounds containing 99.9% silver including;

Arctic Silver 5 that uses three unique shapes and sizes of pure silver particles to maximize particle-to-particle contact area and thermal transfer.

High-Density:

Arctic Silver 5 contains over 88% thermally Conductive filler by weight. In addition to micronized silver, Arctic Silver 5 also contains sub-micron zinc oxide, aluminum oxide and boron nitride particles. These thermally-enhanced ceramic particles improve the compound's performance and long-term stability.

Controlled Triple-Phase Viscosity:

Arctic Silver 5 does not contain any silicone. The suspension fluid is a proprietary mixture of advanced polysynthetic oils that work together to provide three distinctive functional phases. As it comes from the tube, Arctic Silver 5's consistency is engineered for easy application. During the CPU's initial use, the compound thins out to enhance the filling of the microscopic valleys and ensure the best physical contact between the heatsink and the CPU core. Then the compound thickens slightly over the next 50 to 200 hours of use to its final consistency designed for long-term stability.

(This should not be confused with conventional phase change pads that are pre-attached to many heatsinks. Those pads melt each time they get hot then re-solidify when they cool. The viscosity changes that Arctic Silver 5 goes through are much more subtle and ultimately much more effective.)

Not Electrically Conductive:

Arctic Silver 5 was formulated to conduct heat, not electricity.

(While much safer than electrically conductive silver and copper greases, Arctic Silver 5 should be kept away from electrical traces, pins, and leads. While it is not electrically conductive, the compound is very slightly capacitive and could potentially cause problems if it bridges two close-proximity electrical paths.)

The product specification for this micronized silver are as follows:

Thermal Conductance:

>350,000 W/m$^{2\circ}$ C. (0.001 inch layer)

Thermal Resistance:

<0.0045° C.-in$^2$/Watt (0.001 inch layer)

Average Particle Size:

<0.49 microns<0.000020 inch

Extended Temperature Limits:

Peak: −50° C. to >180° C. Long-Term: −50° C. to 130° C.

Performance:

3 to 12 degrees centigrade lower CPU full load core temperatures than standard thermal compounds or thermal pads when measured with a calibrated thermal diode imbedded in the CPU core.

Table 2 shows the raw data for the triplicate counts for all three mouthpieces described above. It should be understood that these were prototype mouthpieces and that the distribution of the micronized silver was not controlled. Therefore, this initial test and manufacturing process provided surface areas where the silver was not evenly distributed, leading to large variability in bacteria counts. The trends, however, are unmistakable, in that the higher concentration of silver particles within the mouthpiece lead to significantly lower bacteria counts as shown in Tables 1 and 2.

TABLE 2

Raw data for triplicate counts for both samples, at 2 time points, inoculated with *Pseudomonas aeruginosa* and *Staphylococcus aureus*. (CFU/mL)

| Sample Identification | Contact time '0 Hours' | | Contact Time '24 Hours' | |
| --- | --- | --- | --- | --- |
| | *P. aeruginosa* CFU/mL | *S. aureus* CFU/mL | *P. aeruginosa* CFU/mL | *S. aureus* CFU/mL |
| #1 (Control) | 67,000,000 | 35,000,000 | 450,000,000 | 476,000,000 |
| | 30,000,000 | 49,000,000 | 632,000,000 | 279,000,000 |
| | 55,000,000 | 27,000,000 | 468,000,000 | 183,000,000 |
| #2 | | | 34,000,000 | 17,500,000 |
| | | | 57,000,000 | 5,300,000 |
| | | | 100,000,000 | 246,000,000 |
| #3 | | | 103,000,000 | 1,700,000 |
| | | | 4,100,000 | 200,000 |
| | | | 22,000,000 | 9,500,000 |

What is claimed is:

1. A dental appliance including a mouthguard, and/or diver's mouthpiece comprising:
   a substantially rigid core that provides a shape to said dental appliance, extending from a proximal in-mouth end toward a position short of a distal outside end and at least one back portion comprising bitewings;
   wherein said dental appliance comprises an elastomeric polymer composition that is intermixed and is an integral mixture with submicron sized metal averaging less than 0.49 microns wherein said metal is in a base of polysynthetic oils and wherein said integral mixture effectively reduces or eliminates the growth of bacterial organisms.

2. The dental appliance of claim 1, wherein said micronized or submicron sized metal is 99.9% pure and is comprised of any of the following including; silver, gold, copper, platinum, and/or organo/inorgano complexes of silver, gold, copper, platinum, aluminum oxide, zinc oxide, boron trinitride and metal or metal oxide and wherein said organo/inorgano complexes include colloidal metals.

3. The dental appliance of claim 1, wherein said diver's mouthpiece comprises a passageway with a U-shaped member that forms the complete mouthpiece of a type with a front portion forming a breathing hole.

4. The dental appliance of claim 1, wherein said elastomeric polymer molded composition comprises liquid silicone rubbers, other silicone elastomers, fluorinated elastomers, thermoplastic elastomers, polyurethanes, composites of polyvinyl chloride, polyethylene, polypropylene and copolymers of polyethylene and polypropylene, composites including $C_{60}$ and wherein said elastomeric polymer composition includes micronized or submicron sized particles of metals or metal complexes.

5. The dental appliance of claim 1, wherein said micronized metal or said submicron sized metal is provided in said base of polysynthetic oils in combination with an injection moldable elastomeric polymer.

6. The dental appliance of claim 1, wherein said submicronized metal is added directly to one or more parts of injection moldable liquid silicone rubber.

7. The dental appliance of claim 1, wherein said dental appliance effectively reduces or eliminates *Staphylococcus aureus* ATCC 6538 and *Pseudomonas aeruginosa* ATCC 15442.

8. A process for making a dental appliance including a mouthguard, and/or diver's mouthpiece comprising:
    forming a substantially rigid core that provides a shape to said dental appliance, extending from a proximal in-mouth end toward a position short of a distal outside end and at least one back portion comprising bitewings;
    wherein said dental appliance comprises an elastomeric polymer composition that is intermixed and is an integral mixture with submicron sized metal less than 0.49 microns wherein said metal is in a base of polysynthetic oils and wherein said integral mixture effectively reduces or eliminates the growth of bacterial organisms.

9. The process of claim 8, wherein said submicron sized metal is 99.9% pure and is comprised of any of the following including; silver, gold, copper, platinum, and/or organo/inorgano complexes of silver, gold, copper, platinum, aluminum oxide, zinc oxide, boron trinitride and wherein said organo/inorgano complexes include colloidal metals.

10. The process of claim 8, wherein said diver's mouthpiece comprises a passageway with a U-shaped member that forms the complete mouthpiece of a type with a front portion forming a breathing hole formed during any molding or extrusion operation.

11. The process of claim 8, wherein said elastomeric polymer molded composition comprises liquid silicone rubbers, other silicone elastomers, fluorinated elastomers, thermoplastic elastomers, polyurethanes, composites of polyvinyl chloride, polyethylene, polypropylene and copolymers of polyethylene and polypropylene, composites including $C_{60}$ and wherein said elastomeric polymer composition includes micronized or submicron sized particles of metals or metal complexes.

12. The process of claim 8, wherein using said dental appliance effectively reduces or eliminates *Staphylococcus aureus* ATCC 6538 and *Pseudomonas aeruginosa* ATCC 15442.

\* \* \* \* \*